(12) United States Patent
Grizzard

(10) Patent No.: US 8,475,497 B2
(45) Date of Patent: Jul. 2, 2013

(54) SPINOUS PROCESS PLATE AND CONNECTOR ASSEMBLY AND METHOD

(75) Inventor: Mark R. Grizzard, Munford, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 127 days.

(21) Appl. No.: 13/276,850

(22) Filed: Oct. 19, 2011

(65) Prior Publication Data
US 2013/0103087 A1    Apr. 25, 2013

(51) Int. Cl.
*A61B 17/70*    (2006.01)

(52) U.S. Cl.
USPC .............. 606/248; 606/247; 606/249

(58) Field of Classification Search
USPC ............ 606/249, 279, 246, 278, 280, 300, 606/250, 248, 262, 282, 289, 291, 247, 264, 606/251–253
See application file for complete search history.

(56) References Cited

U.S. PATENT DOCUMENTS

| | | | |
|---|---|---|---|
| 7,588,592 B2 | 9/2009 | Winslow et al. | |
| 8,002,801 B2 | 8/2011 | Carl et al. | |
| 8,177,814 B2* | 5/2012 | Predick | 606/250 |
| 8,206,420 B2* | 6/2012 | Patel et al. | 606/249 |
| 2008/0114454 A1 | 5/2008 | Peterman et al. | |
| 2008/0183218 A1* | 7/2008 | Mueller et al. | 606/280 |
| 2008/0281359 A1 | 11/2008 | Abdou | |
| 2009/0105766 A1* | 4/2009 | Thompson et al. | 606/279 |
| 2009/0264929 A1 | 10/2009 | Alamin et al. | |
| 2010/0036419 A1 | 2/2010 | Patel et al. | |
| 2010/0114320 A1 | 5/2010 | Lange et al. | |
| 2010/0191288 A1 | 7/2010 | Carl et al. | |
| 2010/0249848 A1 | 9/2010 | Wisnewski et al. | |
| 2011/0029018 A1 | 2/2011 | Carlos | |
| 2011/0071568 A1* | 3/2011 | Ginn et al. | 606/249 |
| 2012/0109202 A1* | 5/2012 | Kretzer et al. | 606/248 |

* cited by examiner

*Primary Examiner* — Pedro Philogene
(74) *Attorney, Agent, or Firm* — Sorell Lenna & Schmidt LLP

(57) ABSTRACT

A spinal implant that includes plates and at least one connector for attachment to spinous processes. The plates may be sized to extend along opposing lateral sides of spinous processes. Connectors may be attached to the plates and extend across the spinous processes. Each of the connectors may be sized and shaped to extend over and across a spinous process and connect the opposing plates together. The connectors may be constructed from a shape-memory material to facilitate attachment with the plates and attachment of the assembly to the spinous processes.

20 Claims, 9 Drawing Sheets

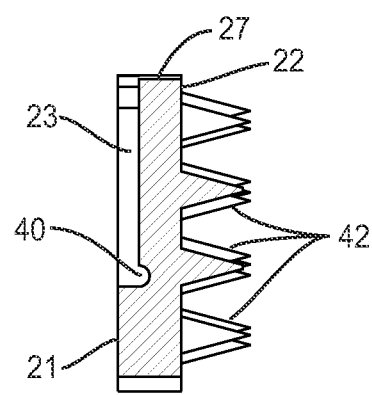 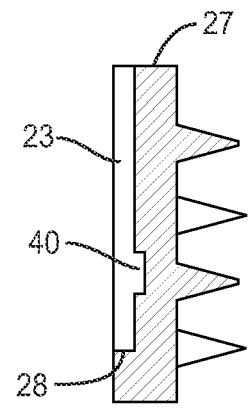
FIG. 5    FIG. 6
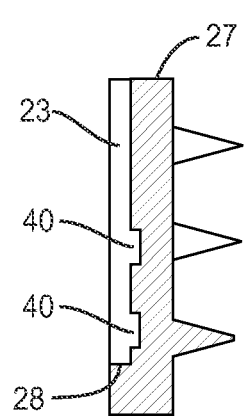 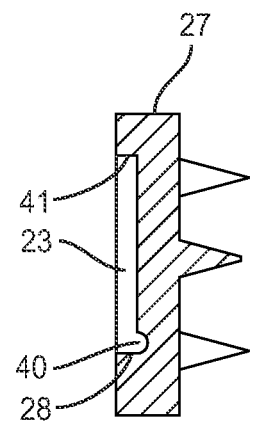
FIG. 7    FIG. 8

SPINOUS PROCESS PLATE AND CONNECTOR ASSEMBLY AND METHOD

BACKGROUND

The present application relates to a spinal implant and a manner of using the same for stabilizing vertebral members, and more particularly, to spinal implants that includes plates and connectors that attach to the spinous processes of the vertebral members.

Vertebral members typically comprise a vertebral body, pedicles, laminae, and processes. The processes are projections that serve as connection points for the ligaments and tendons, and typically include the articular processes, transverse processes, and the spinous process. Intervertebral discs are located between adjacent vertebral bodies to permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

One manner of treating the damage involves mounting a spinal implant onto the spinous processes, typically in association with a fixation process such as anterior lumbar interbody fusion (ALIF), posterior lumbar interbody fusion (PLIF), intertransverse lumbar interbody fusion (ILIF), and the like. While these implants provide some solutions, they may not be ideal for some situations. As such, there remains a need for alternative spinal implants and related methods.

SUMMARY

According to one aspect, a spinal implant for attaching to spinous processes includes a pair of plates sized to extend along the spinous processes. Slots are spaced along the plates and extend into an outer side and a posterior edge of the plates. A first connector is engaged in a first pair of the slots. The first connector extends outward beyond the posterior edge of the plates to extend over a first one of the spinous processes. A second connector is engaged in a second pair of the slots. The second connector extends outward beyond the posterior edge of the plates to extend over a second one of the spinous processes. Each of the first and second connectors are constructed at least in part from a shape-memory material to apply a compressive force to attach the pair of plates to the spinous processes.

The implant may include a first set of teeth that extend outward from an inner side of each of the plates and are aligned with the first pair of slots, a second set of teeth that extend outward from the inner side of each of the plates and are aligned with the second pair of slots, and a non-toothed section on the inner side of each of the plates between the first and second sets of teeth. Each of the first and second connectors may include a pair of legs and an intermediate section, with the intermediate section constructed from the shape-memory material and the legs constructed from a non-memory material. Each of the slots may include an indented section with an increased depth and each of the connectors may include at least two inwardly-extending toes that extend into the indented sections. Each of the plates may include the same shape and size and each of the connectors may include the same shape and size. Each of the connectors may extend along a majority of the height of the plates.

Another aspect includes a spinal implant for attaching to spinous processes that includes a pair of plates sized to extend along the spinous processes. Each of the plates includes: an inner side that faces towards the spinous processes and an outer side that faces away from the spinous processes when the implant is attached to the spinous processes; a posterior edge that faces in a posterior direction and an opposing anterior edge that faces in an anterior direction when the implant is attached to the spinous processes; first and second slots that extend into the outer side and include a bottom end in closer proximity to the anterior edge than the posterior edge with each of the slots further including an indented section with an increased depth; a first section of teeth that extend outward from the inner side and are aligned opposite from the first slot; a second section of teeth that extend outward from the inner side and are aligned opposite from the second slot; and a non-toothed section on the inner side positioned between the first and second sections. The implant also includes first and second connectors that each include first and second legs and an intermediate section that extends between the legs. The legs of the first connector are positioned in the first slots of the plates and the legs of the second connector are positioned in the second slots of the plates. Each of the legs includes an outwardly-extending toe that fits in the indented section of the corresponding slot. The intermediate sections of the connectors are positioned outward beyond the posterior edge of the plates to extend over the spinous processes when the implant is attached to the spinous processes.

The slots of the implant may extend inward through the posterior edge of the plates. The slots may include an enlarged inlet at posterior edge that is wider than a remainder of the slot. The indents may be positioned at the bottom ends of the slots. Each of the first and second connectors may be constructed at least in part from a shape-memory material. The intermediate sections may be constructed from the shape-memory material and the legs are may be constructed from a non-memory metal. The connectors may have a common shape and size and the plates may have a common shape and size. At least one of the slots may include a second indented section that is spaced away from the indented section. At least one of the connectors may include a leg with a second outwardly-extending toe that fits within the second indented section.

Another aspect is directed to a method of stabilizing a spinal section. The method includes positioning a first plate along a first lateral side of first and second spinous processes and a second plate along a second lateral side of the spinous processes. The method includes aligning a first toothed section of each of the first and second plates with the first spinous process and aligning a second toothed section of each of the first and second plates with the second spinous process. The method includes positioning a first connector over the first spinous process and positioning legs of the first connector into first slots in each of the first and second plates with an intermediate section extending outward beyond the plates and over the first spinous process. The method includes positioning a second connector over the second spinous process and positioning legs of the second connector into second slots in each of the first and second plates with an intermediate section extending outward beyond the plates and over the second spinous process. The method includes reducing a size of at least one of the first and second connectors and forcing the plates against the lateral sides of the first and second spinous processes.

The method may further include inserting a toe that extends from each of the legs into and indented section in each of the slots. The method may include that reducing the size of at least one of the first and second connectors and forcing the plates against the lateral sides of the first and second spinous processes comprises heating the connectors that are each constructed at least in part of shape-memory material and reducing a size of the connectors. The method may include reducing an intermediate section of the connectors with a remainder of the connectors maintaining a constant size. The method may include aligning a non-toothed section between the first and second toothed sections of each of the plates with an interspinous space formed. between the first and second spinous processes.

The various aspects of the various embodiments may be used alone or in any combination, as is desired.

BRIEF DESCRIPTION OF THE DRAWINGS

FIG. 5 is a sectional view cut along line V-V of FIG. 4.
FIG. 6 is a sectional view of a plate illustrating a slot.
FIG. 7 is a sectional view of a plate illustrating a slot.
FIG. 8 is a sectional view of a plate illustrating a slot.

DETAILED DESCRIPTION

Figure 1:
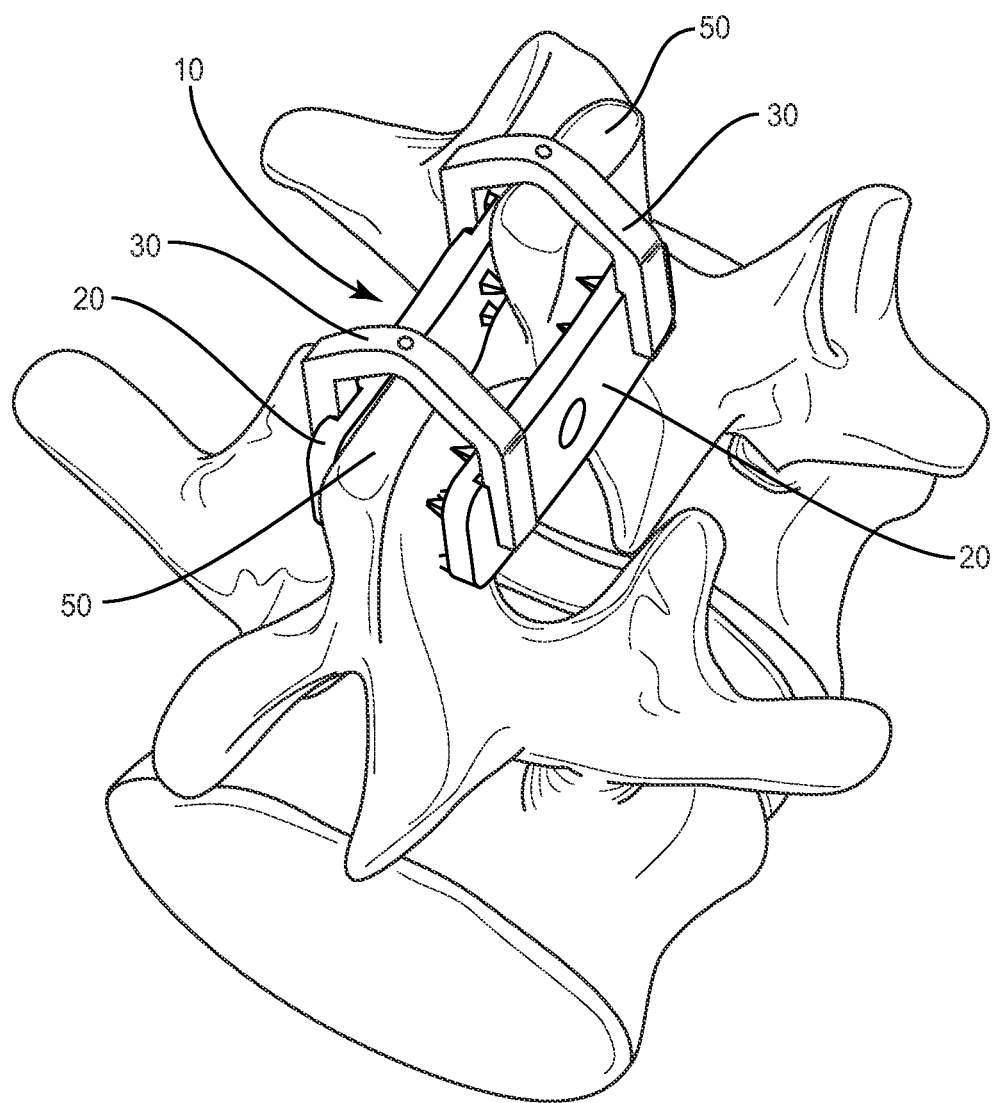
FIG. 1 is a perspective view of a spinal assembly with plates and connectors attached to spinous processes.

The present application is directed to a spinal implant for attachment to spinous processes. The spinal implant includes an assembly of plates positioned along, the spinous processes and connectors that extend between the plates. FIG. 1 illustrates an assembly 10 that includes a pair of plates 20 positioned on opposing lateral sides of spinous processes 50. Connectors 30 are attached to the plates 20 and extend across the spinous processes 50. Each of the connectors 30 is sized and shaped to extend over and across a spinous process 50 and connect the opposing plates 20 together. The connectors 30 may be constructed from a shape-memory material to facilitate attachment with the plates 20 and attachment of the assembly 10 to the spinous processes 50.

Figure 2:
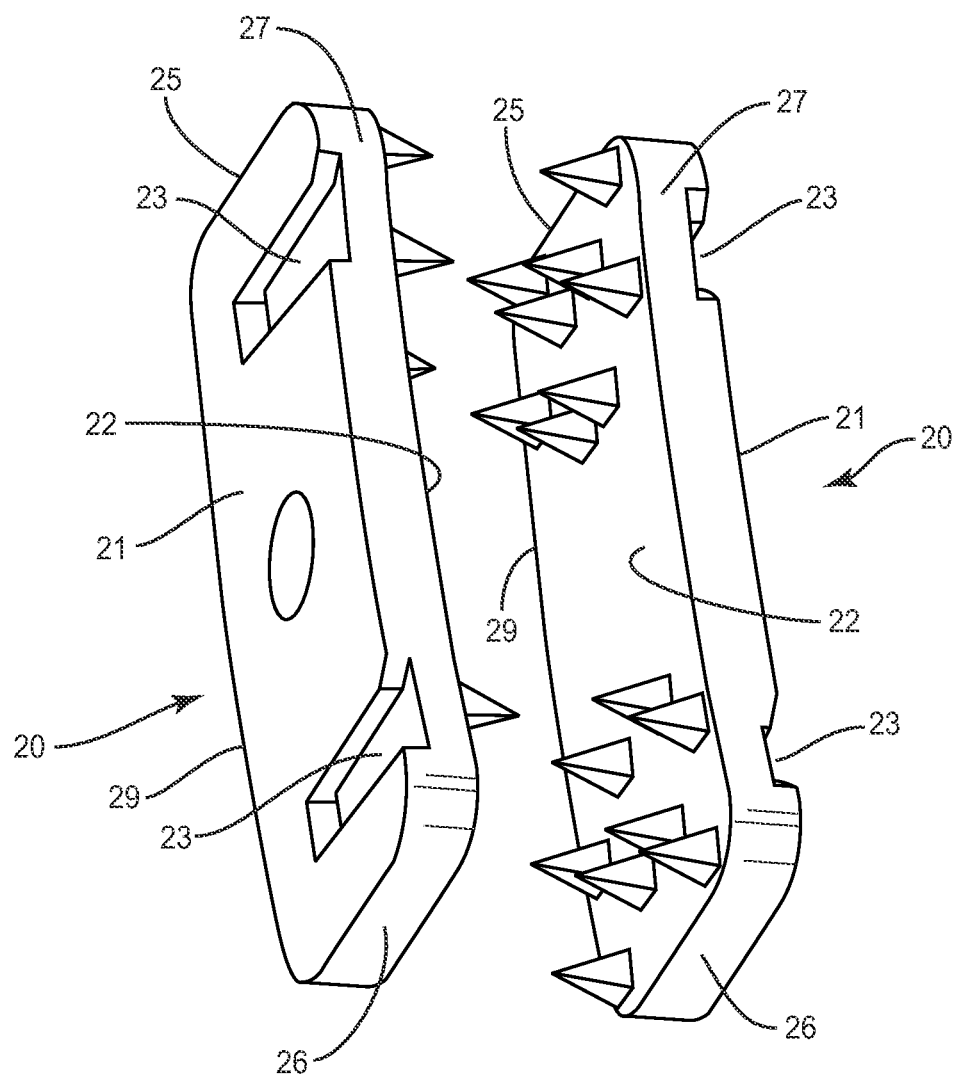
FIG. 2 is a perspective view of a pair of plates.
Figure 3:
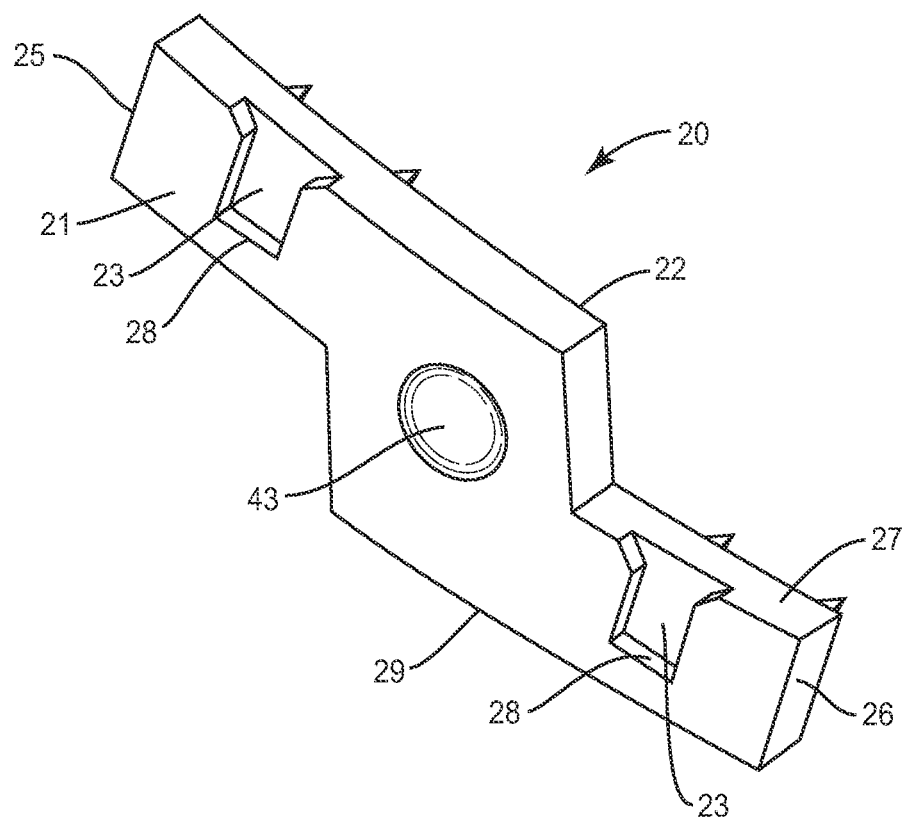
FIG. 3 is a perspective view of a plate.
Figure 4:
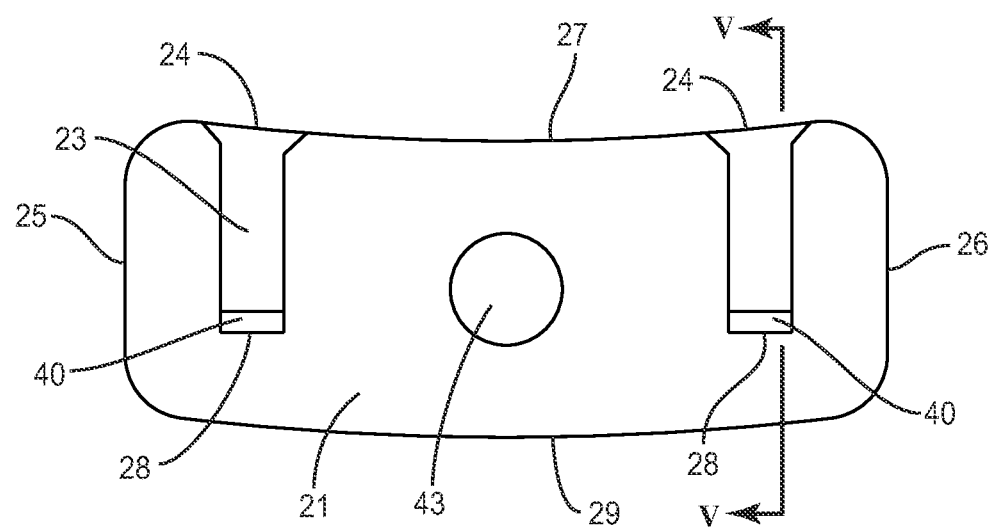
FIG. 4 is a side view of plate.

The plates 20 are sized and shaped to fit along a lateral side of two or more spinous processes 50. As illustrated in FIGS. 2, 3, and 4, the plates 20 include an outer side 21 that faces away from the spinous processes 50 and an opposing inner side 22 that faces towards the spinous processes 50 when attached in the patient. The plates 20 include a length measured between opposing first and second ends 25, 26 that is adequate to span across two or more spinous processes 50. The plates 20 may include various shapes, such as substantially rectangular as illustrated in FIGS. 2 and 4, and a substantially Z-shape as illustrated in FIG. 3.

Slots 23 that receive the connectors 30 are formed on the outer side 21 of the plates 20. In one embodiment as best illustrated in FIGS. 3 and 4, the slots 23 extend into the outer side 21 and the posterior edge 27 of the plates 20. The slots 23 may include an inlet 24 at the posterior edge 27 with an enlarged width to maintain the positioning of the attached connector 30. The remainder of the slot 23 may include a narrower width. The width along the remainder may be substantially constant width as illustrated in FIGS. 3 and 4, or the width may vary. The length of the slot 23 measured between the inlet 24 and the bottom 28 may vary. In some embodiments, the bottom 28 is positioned in closer proximity to the anterior side 29 than the posterior side 27 with the slot 23 extending across a majority of the plate 20.

The depth of the slot 23 into the outer side 21 is adequate to maintain the connector 30. In one embodiment, the depth is substantially constant along the length of the slot 23. The slot 23 may further include an indent 40 to receive a toe 36 that extends outward from the connector 30 to form a more secure connection. The indent 40 includes a greater depth than an adjacent section of the slot 23. In one embodiment, the indent 40 includes the greatest depth within the slot 23. The indent 40 may include various sectional shapes. FIGS. 5 and 8 include an indent 40 having a rounded sectional shape. Indents 40 may also include various other shapes, including a straight back side as illustrated in FIGS. 6 and 7.

The indent 40 may be positioned at various locations along the slot 23. In one embodiment, the indent 40 is located at the bottom 28 of the slot 23 as illustrated in FIGS. 4, 5 and 8. Other embodiments may locate the indent 40 away from the bottom 28, such as at an intermediate location along the slot 23 as illustrated in FIG. 6. The slot 23 may also include multiple indents 40 as illustrated in FIG. 7. The different indents 40 may include the same or different shapes and/or sizes. The multiple indents 40 may in close proximity or spaced apart along the length of the slot 23.

In one embodiment, the slot 23 extends inward through the posterior edge 27 of the plate 20 such as illustrated in FIGS. 2, 3, 4, 5, 6, and 7. The slot 23 may also be spaced away from the posterior edge 27 as illustrated in FIG. 8. This embodiment of the slot 23 includes a top 41 opposite from the bottom 28. The distance the top 41 is spaced away from the posterior edge 27 may vary depending upon the context of use. The top 41 may engage with the connector 30 similar to the indent 40 and function to facilitate a secure connection.

The plates 20 also include teeth 42 that extend outward from the inner side 22 to engage with the spinous processes 50. The shape and length of the teeth 42 may vary. Each of the teeth 42 may include the same or different shapes and/or sizes.

Figure 9:
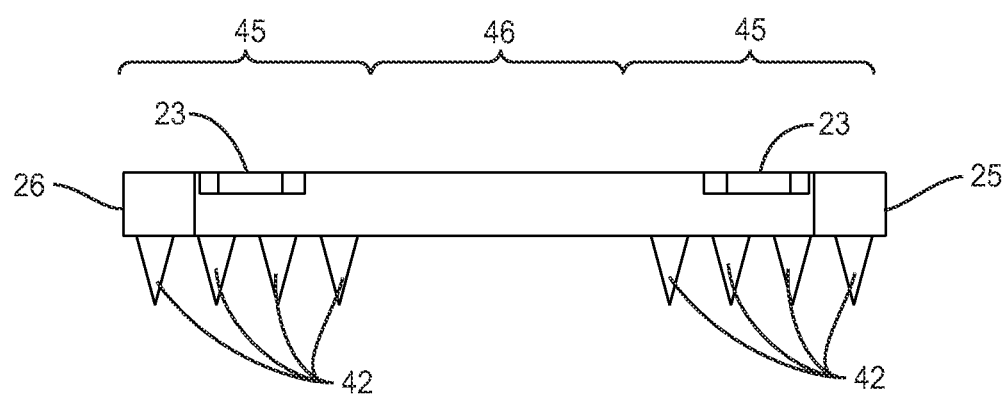
FIG. 9 is a top view of a plate.

The teeth 42 are located within one or more toothed sections 45 located along a limited length of the plate 20 as illustrated in FIG. 9. The length of each of the toothed sections 45 extends between the outer-most teeth 42. The different sections 45 may include the same or different lengths. The toothed sections 45 are located on an opposing side of the plate 20 from the slots 23. This positioning provides for the compressive force applied by the corresponding connector 30 to facilitate engaging the teeth 42 with the spinous processes 50. In one embodiment, the slot 23 is centered within the toothed section 45. A non-toothed section 46 is positioned between the toothed sections 45. The non-toothed section 46 is positioned away from the slots 23 and may be aligned with the interspinous space 51 formed between the spinous processes 50.

One or more receptacles 43 may extend into the outer side 21 of the plates 20. The receptacles 43 are configured to engage with tools for positioning the plate 20 within the patient and attaching the plate 20 to the spinous processes 50. The receptacles 43 may include various different shapes and sizes. In one embodiment as illustrated in FIGS. 3 and 4, the receptacles 43 include a semi-spherical shape.

In one embodiment, each of the plates 20 includes at least one receptacle 43 that is positioned along a central region between the first and second ends 25, 26. The receptacles 43 may also positioned between the toothed sections 45. In one embodiment, the plates 20 are aligned on opposing sides of the spinous processes 50 with the receptacles 43 being aligned. A compression tool that includes a pair of engagement members is applied to the plates 20 with a first engagement member positioned in the receptacle 43 of the first plate 20 and a second engagement member in the receptacle 43 of the second plate 20. The compression tool applies a compression force to the plates 20 to engage the spinous processes 50.

The plates 20 may be made of various suitable biocompatible materials. Suitable biocompatible materials include, but are not limited to, one or a combination of the following: metals such as titanium alloys, commercially available titanium, stainless steel, cobalt chrome ("CoCr") and polymers such as polyetheretherketone ("PEEK"), ultra high molecular weight polyethylene ("UHMWPE") and polyethylene.

Figure 10:
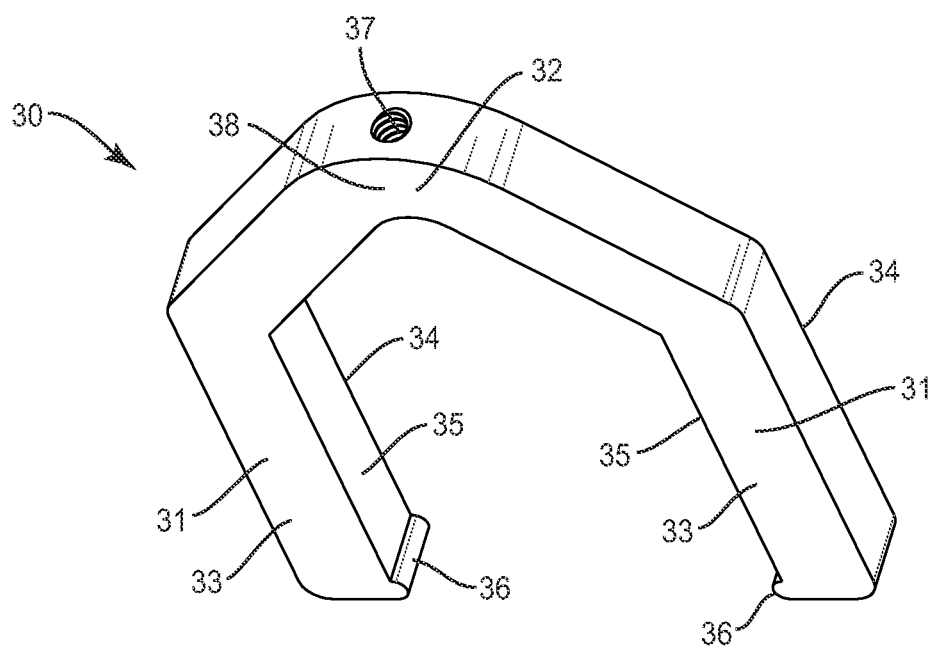
FIG. 10 is a perspective view of a connector.
Figure 11:
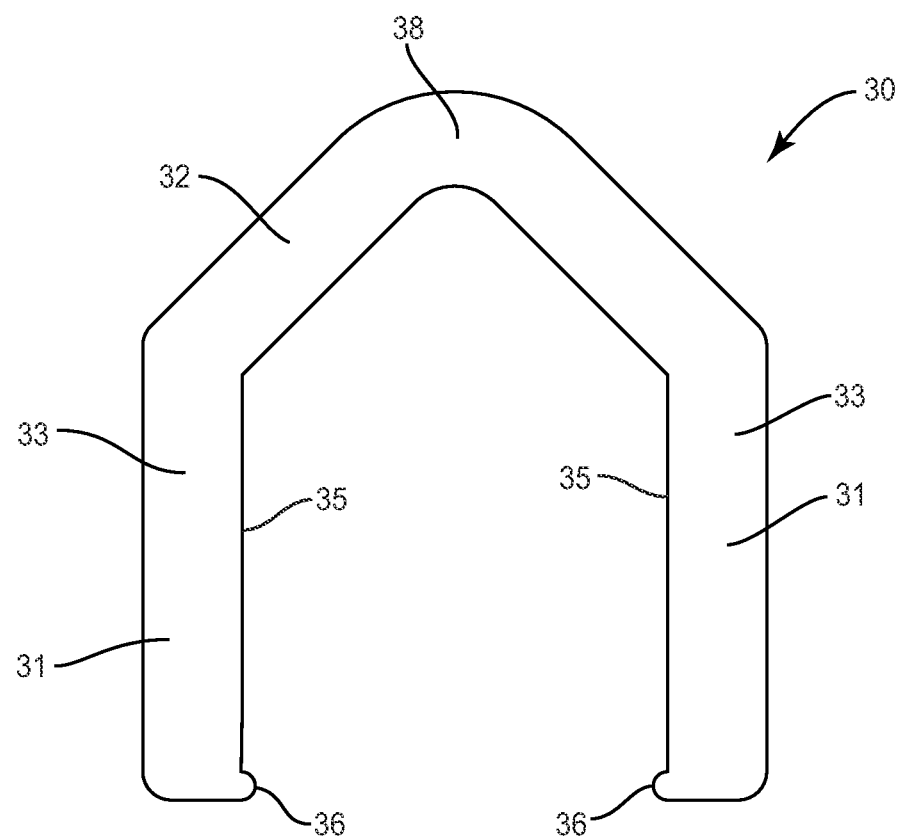
FIG. 11 is a side view of a connector.

One or more connectors 30 extend between and connect the plates 20 together. FIGS. 10 and 11 include a connector 30 with a pair of legs 31 and an intermediate section 32. The legs 31 are sized to fit within the corresponding slots 23 of the plates 20. The legs 31 include a width measured between opposing first and second sides 33, 34. The width is less than the width of the slots 23 for the legs to fit within the slots 23. The legs 31 further include an inner side 35 that contacts against the plate 20. The two legs 31 may include the same or different shapes and/or sizes. In one embodiment, the inner sides 35 of each of the legs 31 are substantially flat and parallel to each other.

At least one toe 36 extends outward from the inner side 35 of each leg 31 to engage with the corresponding indent 40 in the slot 23. The shape of the toe 36 may correspond to the shape of the indent 40. FIGS. 10 and 11 each include toes 36 with a rounded shape that match a rounded indent 40 as illustrated in FIG. 5. The toe 36 may also include a rectangular shape to match the indent 40 as illustrated in FIGS. 6 and 7. The toe 36 may be positioned at various locations along the leg 31. In one embodiment, the toe 36 is positioned at an end of the leg 31 as illustrated in FIGS. 10 and 11.

In one embodiment, the legs 31 each include a single toe 36. Other embodiments include two or more toes 36 extending outward from the inner side 35. The toes 36 on a leg 31 may have the same or different shapes and/or sizes. Further, the two legs 31 may include different numbers and different shapes and sizes of toes 36. By way of example, a first leg 31 may include a single rounded toe 36, and a second leg 31 may include two rectangular toes 36.

Figure 12:
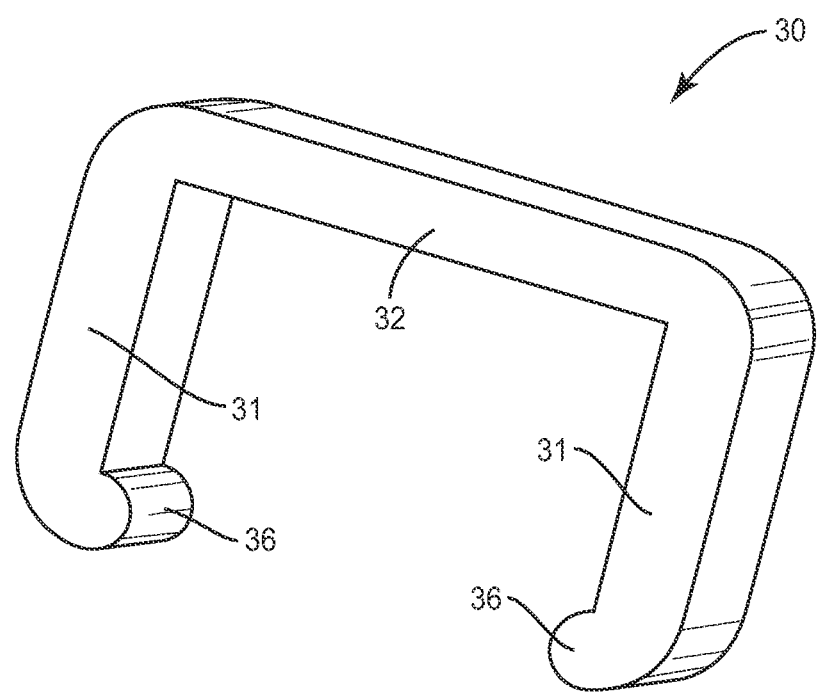
FIG. 12 is a perspective view of a connector.

The intermediate section 32 extends between the legs 31. As best illustrated in FIG. 1, the intermediate section 32 is sized to extend outward beyond the sides of the plates 20 and over a spinous process 50. The shape of the intermediate section 32 may vary. FIGS. 10 and 11 include an arch shape with a central peak 38. The peak 38 is positioned half-way between the legs 31 to be aligned over the spinous process 50. FIG. 12 includes an intermediate section 32 that is substantially straight.

A mount 37 may be positioned along the intermediate section 32. The mount 37 functions to receive a tool for positioning the connector 30 in the patient. FIG. 10 includes the mount 37 being a threaded cavity to receive a tool and is positioned at the peak 38.

In one embodiment, the connector 30 is at least partially formed of shape-memory material that exhibits pseudoelastic or superelastic characteristics or behavior at about human body temperature. The connector 30 includes a first shape when it is initially inserted into the patient, and a second memorized shape. The first shape may include a larger distance between the legs 31 than the second shape. This first shape provides for positioning the legs 31 within the corresponding slots 23 in the plates 20 and the intermediate section 32 across the spinous process 50. The second memorized shape may include a smaller distance between the legs for the connector 30 being sized to apply a compressive force to the plates 20. This force attaches and maintains the attachment of the plates 20 to the spinous processes 50.

The connector 30 may be constructed from a variety of shape-memory materials. Examples include shape-memory metal alloys (e.g., alloys of known metals, such as, for example, copper and zinc, nickel and titanium, and silver and cadmium) and shape-memory polymers. While there are many alloys which exhibit shape-memory characteristics, one is a Nitinol which is an alloy of nickel and titanium. Nitinol is well suited for the particular application of the connector 30 because it can be programmed to undergo a stress-induced martensitic transformation at about normal human body temperature (i.e., at about 35-40 degrees Celsius).

In one embodiment, the entire connector 30 is constructed from shape-memory material. In other embodiments, the connector 30 is only partially constructed from shape-memory material with one or more sections constructed from non-memory material. In one specific embodiment, the intermediate section 32 is constructed from shape-memory material and the legs 31 are constructed from non-memory material. The non-memory portions may be constructed from a biocompatible material, such as, for example, a carbon fiber material, or non-metallic substances, including polymers or copolymers made from materials such as PEEK and UHMWPE. In further embodiments, the non-expanding portions may be formed of other suitable biocompatible materials, such as, for example, stainless steel, titanium, and cobalt-chrome. In one embodiment, the non-memory material is the same shape-memory material as the deforming portion that is configured to maintain its shape. This non-memory material with the same construction as the memory-material includes a rigid geometry that resists compression, even when the material is chilled or stressed.

In embodiments with the implant assembly 10 including two or more connectors 30, the different connectors 30 may include the same Or different constructions. In one embodiment, a single one of the connectors 30 is constructed from shape-memory material with the other one or more connectors 30 being constructed from non-memory material. Other embodiments include multiple connectors 30 constructed from shape-memory material. These multiple connectors 30 may include the same or different shape-memory material configurations. In one embodiment, the different connectors 30 are made from different shape-memory materials. In another embodiment, different sections of the different connectors 30 are constructed from shape-memory material. In another embodiment, each of the connectors 30 includes the same construction.

The implant assembly 10 may include plates 20 that have the same shape and size. The plates 20 may also include different shapes and/or sizes. The connectors 30 may each have the same shape and size, or different connectors 30 may include different shapes and/or sizes. Further, the different plates 20 and different connectors 30 may each have the same construction, or may have different constructions.

In use, the plates 20 are implanted into the patient and positioned along opposing lateral sides of the spinous processes 50. The teeth 42 that extend outward from the inner side 35 of each of the plates 20 are aligned with the spinous processes 50. This positioning also aligns the slots 23 on the opposing outer side 21 of the plates 20 with the spinous processes 50. In one embodiment, each of the plates 20 includes the same shape and size with the first and second ends 25, 26 being aligned along the spine.

In one embodiment, a compression tool is inserted into the patient. The compression tool engages with the receptacles 43 on the outer sides 21 of the plates 20. The compression tool applies a compressive force to the plates 20 to engage the teeth 42 with the spinous processes 50.

The connectors 30 are inserted into the patient. Each of the connectors 30 may be inserted at the same time, or may be serially inserted into the patient. In one embodiment, a first connector 30 is initially inserted into the patient and aligned and attached with the first and second plates 20, followed by the one or more subsequent connectors 30.

During insertion, the connectors 30 are aligned with the corresponding slots 23 in the plates 20. The legs 31 of the first connector 30 are aligned with the first slots 23 in the first and second plates 20. In one embodiment, the legs 31 are aligned with the enlarged inlets 24 in the slots 23. The legs 31 are then slid down into the slots 23. The one or more toes 36 that extend outward from the inner sides 35 of the legs 31 may further engage with the corresponding indents 40 in the slots 23. In one embodiment, the connector 30 is inserted into the slots 23 until the one or more toes 36 engage in the corresponding indents 40. In another embodiment, the connectors 30 are inserted into the slots 23 until an end of the connectors 30 contacts against the bottom 28 of the slots 23.

The other one or more connectors are inserted into the patient and the slots 23 in a similar manner. The legs 31 of the second connector 30 are aligned with the second slots 23 in the plates 20. The connector 30 is then slid into the plates 20 with the legs 31 sliding along the slots 23 until the one or more toes 36 engage into the indents 40 or the end of the legs 31 contacts against the bottom 28 of the slot 23. Likewise, any additional connectors 30 are aligned and inserted into the additional slots 23 in the plates 20.

Once the connectors 30 are positioned as desired, exposure to body temperatures (or locally applied heat) cause the shape-memory material to apply a compressive force to the plates 20. The shape-memory material returns towards a shape that reduces a distance between the legs 31. This change causes the legs 31 to apply a compressive force against the plates 20 to engage the plates 20 with the spinous processes 50. In one embodiment, a single connector 30 applies the compressive force to the plates 20. In another embodiment, two or more of the connectors 30 are constructed from shape-memory material and apply a compressive force to the plates 20.

In one embodiment, each of the connectors 30 are positioned in the patient and attached to the plates 20 prior to the application of the compressive force(s) from the one or more connectors 30. In another embodiment, the connectors 30 are serially implanted and attached to the plates 20. The just-inserted connector 30 is allowed to re-shape and apply a compressive force prior to insertion and attachment of the next connector 30.

In one embodiment, the initial shape of the connectors 30 prior to deformation provides for insertion into the slots 23 and engagement of the toes 36 into the corresponding indents 40. In another embodiment, the initial size is large enough that the legs 31 do not engage into the slots 23 until after the deformation. In another embodiment, the legs 31 are engaged into the slots 23 when the connectors 30 are initially in the first shape. The engagement between the toes 36 and indents 40 does not occur until after deformation towards the second shape.

While the implant assemblies 10 and methods described above have been discussed in the context of implantation within a living patient for the treatment of various spinal disorders, such is not required. Indeed, the various assemblies and methods described herein may also be used in a non-living situation, such as within a cadaver, model, and the like. The non-living situation may be for one or more of testing, training, and demonstration purposes.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A spinal implant for attaching to spinous processes comprising:
    a pair of plates sized to extend along the spinous processes and including a plurality of slots spaced along the plates that extend into an outer side and a posterior edge of the plates;
    a first connector engaged in a first pair of the slots, the first connector extending outward beyond the posterior edge of the plates to extend over a first one of the spinous processes;
    a second connector engaged in a second pair of the slots, the second connector extending outward beyond the posterior edge of the plates to extend over a second one of the spinous processes;
    each of the first and second connectors constructed at least in part from a shape-memory material to apply a compressive force configured to attach the pair of plates to the spinous processes.

2. The implant of claim 1, further comprising a first set of teeth extending outward from an inner side of each of the plates and aligned with the first pair of slots, a second set of teeth extending outward from the inner side of each of the plates and aligned with the second pair of slots, and a non-toothed section on the inner side of each of the plates between the first and second sets of teeth.

3. The implant of claim 1, wherein each of the first and second connectors include a pair of legs and an intermediate section, with the intermediate section constructed from the shape-memory material and the legs constructed from a non-memory material.

4. The implant of claim 1, wherein each of the slots includes an indented section with an increased depth and each of the connectors includes at least two inwardly-extending toes that extend into the indented sections.

5. The implant of claim 1, wherein each of the plates includes the same shape and size and each of the connectors includes the same shape and size.

6. The implant of claim 1, wherein each of the connectors extends along a majority of the height of the plates.

7. A spinal implant for attaching to spinous processes comprising:
- a pair of plates sized to extend along the spinous processes, each of the plates including:
  - an inner side that faces towards the spinous processes and an outer side that faces away from the spinous processes when the implant is attached to the spinous processes;
  - a posterior edge that faces in a posterior direction and an opposing anterior edge that faces in an anterior direction when the implant is attached to the spinous processes;
  - first and second slots that extend into the outer side and including a bottom end in closer proximity to the anterior edge than the posterior edge, each of the slots further including an indented section with an increased depth;
  - a first section of teeth that extend outward from the inner side and are aligned opposite from the first slot;
  - a second section of teeth that extend outward from the inner side and are aligned opposite from the second slot;
  - a non-toothed section on the inner side positioned between the first and second sections;
- first and second connectors that each include first and second legs and an intermediate section that extends between the legs, the legs of the first connector are positioned in the first slots of the plates and the legs of the second connector are positioned in the second slots of the plates, each of the legs including an outwardly-extending toe that fits in the indented section of the corresponding slot, the intermediate sections of the connectors positioned outward beyond the posterior edge of the plates to extend over the spinous processes when the implant is configured to attach to the spinous processes.

8. The implant of claim 7, wherein the slots extend inward through the posterior edge of the plates.

9. The implant of claim 8, wherein the slots include an enlarged inlet at posterior edge that is wider than a remainder of the slot.

10. The implant of claim 7, wherein the indents are positioned at the bottom ends of the slots.

11. The implant of claim 7, wherein each of the first and second connectors is constructed at least in part from a shape-memory material.

12. The implant of claim 11, wherein the intermediate sections are constructed from the shape-memory material and the legs are constructed from a non-memory metal.

13. The implant of claim 7, wherein the connectors have a common shape and size and the plates have a common shape and size.

14. The implant of claim 7, wherein at least one of the slots includes a second indented section that is spaced away from the indented section.

15. The implant of claim 14, wherein at least one of the connectors includes a leg with a second outwardly-extending toe that fits within the second indented section.

16. A method of stabilizing a spinal section comprising:
- positioning a first plate along a first lateral side of first and second spinous processes and a second plate along a second lateral side of the spinous processes;
- aligning a first toothed section of each of the first and second plates with the first spinous process and aligning a second toothed section of each of the first and second plates with the second spinous process;
- positioning a first connector over the first spinous process and positioning legs of the first connector into first slots in each of the first and second plates with an intermediate section extending outward beyond the plates and over the first spinous process;
- positioning a second connector over the second vinous process and positioning legs of the second connector into second slots in each of the first and second plates with an intermediate section extending outward beyond the plates and over the second spinous process; and
- reducing a size of at least one of the first and second connectors and forcing the plates against the lateral sides of the first and second spinous processes.

17. The method of claim 16, further comprising inserting a toe that extends from each of the legs into an indented section in each of the slots.

18. The method of claim 16, wherein reducing the size of at least one of the first and second connectors and forcing the plates against the lateral sides of the first and second spinous processes comprises heating the connectors that are each constructed at least in part of shape-memory material and reducing a size of the connectors.

19. The method of claim 18, further comprising reducing an intermediate section of the connectors with a remainder of the connectors maintaining a constant size.

20. The method of claim 16, further comprising aligning a non-toothed section between the first and second toothed sections of each of the plates with an interspinous space formed between the first and second spinous processes.

* * * * *